United States Patent [19]
Manes et al.

[11] Patent Number: 5,868,742
[45] Date of Patent: Feb. 9, 1999

[54] AUXILIARY REFERENCE ELECTRODE AND POTENTIAL REFERENCING TECHNIQUE FOR ENDOSCOPIC ELECTROSURGICAL INSTRUMENTS

[75] Inventors: Michael R. Manes, Littleton, Colo.; John Gentelia, Madison, N.Y.

[73] Assignee: Conmed Corporation, Utica, N.Y.

[21] Appl. No.: 544,735

[22] Filed: Oct. 18, 1995

[51] Int. Cl.$^6$ ................................................ A61B 17/36
[52] U.S. Cl. ............................ 606/46; 606/41; 606/42; 606/47
[58] Field of Search .................... 606/32–35, 41

[56] References Cited

U.S. PATENT DOCUMENTS

| | | | |
|---|---|---|---|
| 4,416,277 | 11/1983 | Newton et al. | 606/35 |
| 5,135,506 | 8/1992 | Gentelia et al. | |
| 5,312,401 | 5/1994 | Newton et al. | |

OTHER PUBLICATIONS

Health Devices, vol. 24, No. 1, Jan., 1995, pp. 1–40.
C. Randle Voyles, M.D., et al., *Trocar/Cannula Systems in Laparoscopic Surgery*, Surgical Rounds, Sep., 1992, pp. 799–804.
C. Randle Voyles, M.D., et al., *Education and Engineering Solutions for Potential Problems with Laparoscopic Monopolar Electrosurgery*, The American Journal of Surgery, vol. 164, Jul. 1992, pp. 57–62.
Electrosurgical EM–1 Monitor System Brochure, Electroscope, Inc., 1991.
Valleylab Instruction Manual; Valleylab, Inc., 1980, pp. 2–8, 2–9, 9–7.
Olympus UES–10 Brochure, prior to Oct. 18, 1994.

*Primary Examiner*—David M. Shay
*Attorney, Agent, or Firm*—John R. Ley

[57] ABSTRACT

Non-insulated surgical instruments are referenced to the electrical potential of a patient during minimally invasive electrosurgery to prevent unintentional patient burns, should the surgical instruments become accidentally energized during the electrosurgical procedure. An auxiliary safety electrode separate from the primary return electrode is attached to the patient at a location separate from the attachment point of the primary return electrode. Each non-insulated surgical instrument is preferably attached to the auxiliary electrode by a separate electrical conductor. The electrical conductor transfers to the auxiliary electrode any electrical energy which is accidentally applied to the instrument during the course of the electrosurgical procedure. The size of the auxiliary electrode is sufficient to safely disperse the electrical charge without burning the patient. When used with conductive cannulas, the electrical conductor is attached between the metal cannula and the auxiliary electrode to dissipate any electrical energy unintentionally transferred to the metal cannula. The auxiliary electrode does not interfere with the operation of a split return electrode or any contact quality monitoring system which monitors the integrity of the contact between the primary return electrode and the patient.

30 Claims, 7 Drawing Sheets

AUXILIARY REFERENCE ELECTRODE AND POTENTIAL REFERENCING TECHNIQUE FOR ENDOSCOPIC ELECTROSURGICAL INSTRUMENTS

This invention relates to endoscopic monopolar electrosurgery, and more particularly to a new and improved apparatus and method for connecting instruments and apparatus used during the endoscopic procedure to a reference potential of the patient, thereby substantially reducing the possibilities of unintentional burns to the patient and to the surgical personnel performing the procedure.

BACKGROUND OF THE INVENTION

Endoscopic surgery involves inserting surgical instruments through small incisions to perform a surgical procedure on the interior organs and tissues. By using these instruments in this manner, it is not necessary to create a large open incision to gain access to the organs and tissues. In this regard endoscopic surgery is regarded as minimally invasive.

Although there are many types of endoscopic surgical procedures, the present invention will be described with respect to a laparoscopic procedure conducted within a patient's abdominal cavity. Of course, the scope of the present invention is not limited to such laparoscopic procedures.

To access the internal organs and tissues and to provide adequate space for conducting the surgical procedure, the abdominal or other body wall is distended away from the tissues and organs by pressurizing the abdominal or other internal cavity. A viewing device known as a laparoscope and a light source are inserted into the abdominal cavity to allow the surgeon to view the surgical site and the surgical effects created by use of the instruments. Most present laparoscopes typically include a miniature electronic video camera by which to view the surgical site with a monitor.

The typical surgical instruments used during the laparoscopic procedure are both mechanical and electrosurgical. Mechanical laparoscopic surgical instruments include knives, snares and graspers which are attached to the ends of relatively long manipulating tools. Electrosurgical instruments generally take the form of one or more relatively long, insulated electrodes through which high frequency, high voltage electrical current is delivered to cut tissue, coagulate bleeding from the tissue or to cut and coagulate simultaneously at the surgical site.

The surgical instruments and laparoscope are inserted into the abdominal cavity through cannulas. A cannula is a tube-like device which extends through an incision formed in the abdominal wall. An interior opening in the cannula allows the surgical instruments and other accessories to pass from the exterior of the patient into the abdominal cavity. The interior opening of the cannula also includes a sealing device to prevent the escape of the pressurized gas from within the abdominal cavity.

Laparoscopic electrosurgical procedures present increased possibilities for unintended electrical burns to the patient and to the attending surgical personnel, compared to typical open electrosurgical procedures. In general, unintended burns result from the fact that the electrosurgical current flows in a path which is not intended, obvious, anticipated or consistent. Protective equipment has been devised to eliminate and avoid unintended burns in open electrosurgical procedures, and some of this protective equipment, such as a return electrode contact quality monitor, is useful and desirable during laparoscopic electrosurgical procedures. However, adequate protective equipment to guard against the causes of unintended burns during laparoscopy has not previously been available. Indeed, some of the leading causes of unintended burns during laparoscopy appear not to be fully understood or appreciated.

Practical considerations that increase the possibilities of unintended burns during laparoscopic procedures (compared to open electrosurgery) include: the requirement that high frequency, high voltage electrical current must pass through the cannula; the limitation on the observation area within the abdominal cavity to that which is illuminated; and the restriction that interaction with the tissues and organs can occur only through the instruments inserted through the cannula.

If the cannula becomes electrically charged as a result of electrical energy being transferred from the electrode to the cannula during electrosurgery, and if the cannula is the typical uninsulated metal type which is in direct contact with the abdominal wall at the insertion site, the cannula will conduct the current into the abdominal wall. A void, separation or break in the insulation of the electrosurgical electrode may allow the cannula to become unintentionally charged if the defect in the insulation is located within the length of the cannula. Additionally, even if the electrode insulation is undamaged, the relatively high frequency electrosurgical current will capacitively couple from the electrode to the closely adjacent metal cannula, thereby electrically charging the cannula. The metal cannula can also become electrically charged if the active end of the electrosurgical electrode inadvertently contacts the cannula within the abdominal cavity while electrosurgical current is delivered to the electrode.

With respect to the restricted view of the surgical site within the abdominal cavity, not only is the view limited to the area illuminated by the small light source, but the viewing perspective within the abdominal cavity is limited to a two dimensional view from the laparoscope. Without the third dimension to provide viewing perspective or depth of field, the active end of the electrode can be erroneously positioned while electrosurgical current is being delivered. A mistakenly positioned electrode can cause burns in unintended locations. Furthermore, the limited viewing area resulting from the limited illumination and camera angle may fail to reveal that some of the instruments are incorrectly positioned or that the instruments are positioned in a location which will result in inadvertent contact with the active electrode. Inadvertent contact between a metal instrument and the active electrode can electrically charge the instrument, and contact of that charged instrument with the tissue or organs can cause unintended burns.

Similarly, when the tissue or organs are held with graspers or are otherwise contacted by an instrument and electrosurgical current is applied, there is a possibility that the current return path through the held or contacted tissue will include the graspers or instruments and the surgical personnel manipulating the graspers or other instruments. The possibility of an unintentional return path through the graspers or other contacted instruments increases substantially as the tissue is severed from the patient. As the tissue is severed, the return path through the patient decreases in size and therefore increases in impedance, thereby increasing the chance of an unintended return path through the grasper and the person holding the grasper.

Furthermore, in addition to causing unintentional patient burns, contact with the active electrode may damage many present laparoscopic surgical instruments. For example, many present laparoscopes include electronic circuitry such as an IC chip within the instrument housing to provide the ability to send video images to a monitor in the operating room. Such circuitry is susceptible to electrical interference and may be irreparably damaged should the laparoscope become unintentionally charged during the minimally invasive procedure.

To address some of these risks and concerns, it has been strongly recommended that only electrically conductive (i.e., metal) cannulas be employed in laparoscopic electrosurgery. This recommendation is based on the assumption that a metal or electrically conductive cannula will harmlessly dissipate unintentional electrical charges to the abdominal wall. The size of the metal cannula and the thickness of the abdominal wall has been regarded as sufficient to safely dissipate any current without creating patient burns. By discharging the unintentional current from the cannula into the abdominal wall in this manner, the risk of unintentional burns from an electrically charged cannula is thought to be avoided. However, it has been found that when a metal cannula is directly coupled to the active electrode (such as by direct contact with the electrode tip or through insulation failure), the current discharged through the cannula can injure the abdominal wall tissue at the site where the cannula is inserted through the abdominal wall.

As an adjunct to the recommendation that only metal conductive cannulas be used, it has been recommended that plastic nonconductive cannulas and plastic nonconductive retaining devices for metal cannulas not be used. Plastic cannulas will not conduct electrical charges into the abdominal wall, thereby preventing a return path through the abdominal wall for any unintended electrical charge. Similarly, the use of plastic retention devices which insulate metal cannulas from the abdominal wall has also been discouraged. Plastic retention devices prevent the discharge of any unintended electrical charge to the abdominal wall. When the metal cannula is insulated from the abdominal wall by the plastic retention device, there is an increased possibility that the inner end of the metal cannula within the abdominal cavity might contact a tissue or organ and thereby discharge at that location causing an unintended burn. The inner end of the cannula frequently rests against interior organs is easily moved into such a position because of the flexibility of the abdominal wall. A burn from an unintentional contact of the inner end of a charged cannula with the bowel can cause a perforation of the bowel, leading to dangerous consequences.

Other recommendations for reducing unintentional burns relate to improving laparoscopic surgical technique. For instance, care should be taken to avoid unintentionally contacting the active electrode with other instruments and with tissues during the surgical procedure. Additionally, electrical energy should only be delivered to the active electrode when the position of the active electrode has been confirmed. Furthermore, the light source should be accurately positioned to illuminate all the relevant areas within the abdominal cavity.

One piece of existing equipment directed to resolving some of the concerns of unintended burns during laparoscopic electrosurgery, disclosed in U.S. Pat. No. 5,312,401 to Newton et al. for an ELECTROSURGICAL APPARATUS FOR LAPAROSCOPIC AND LIKE PROCEDURES, utilizes a shield that slides over the active electrode before it is extended into the abdominal cavity through the cannula. A monitor attached to the shield monitors the level of current coupled to the shield and disables the electrosurgical generator if an unacceptable level of current is coupled to the cannula. While this device appears to be effective in resolving problems of capacitive coupling and insulation failure when used with a metal cannula, it is not effective in resolving many of the other concerns associated with laparoscopic electrosurgery. For example, the device will not prevent the unintentional energization of other instruments not associated with the active electrode, such as mechanical graspers. Furthermore, the device is relatively expensive and presents additional issues of complexity in equipment use during surgery.

A relatively old technique suggested for use in urinary procedures is to attach a ground wire between a colonoscope and the electrosurgical generator to prevent the surgeon from burning his eye while peering through the eyepiece of the colonoscope. Such a system is not intended to prevent unintentional patient burns and will not prevent other laparoscopic instruments from being accidentally energized.

It is with respect to these and other considerations that the present invention for eliminating or reducing the possibility of unintended burns to the patient and the surgical personnel during laparoscopic electrosurgery has evolved.

SUMMARY OF THE INVENTION

One of the important discoveries associated with the present invention is that the dissipation of electrical energy coupled to a metal cannula inserted through the abdominal wall at the insertion site may indeed create unintended patient burns at the abdominal wall. This discovery suggests that the problem of unintended patient burns at the abdominal wall is considerably greater than previously anticipated, thereby increasing the significance of the present invention in the field of laparoscopic electrosurgery and diminishing the value of the previously suggested safety techniques which rely on the conductivity of a metal cannula with the abdominal wall.

Another important aspect of the present invention is that plastic or other non-conductive cannulas, when used in conjunction with the present invention, offer substantial capabilities for eliminating many of the previous risks and concerns which were previously believed to be resolved only from better and more careful surgical technique. For example, the use of plastic cannulas with the present invention provides better safety and avoids the possibility of any discharge of electrical current from the inner end of the cannula at an unintended or unobserved location.

A further aspect of the present invention is that plastic retaining devices for metal cannulas will avoid unintentional patient burns to the abdominal wall or to an internal tissue or organ from the inner end of the metal cannula. Use of the present invention with a metal cannula and a plastic retaining device is effective in eliminating the risks of unintended burns to any surgical personnel who happen to contact the cannula.

Another significant aspect of the present invention relates to referencing all laparoscopic instruments to a reference potential with a technique which maintains the effectiveness of all known return electrode contact quality monitors, thereby obtaining return electrode safety monitoring while preserving the important functionality of those devices during laparoscopic electrosurgery.

In accordance with these discoveries and features, an auxiliary electrode is connected to the patient separately from the normal or primary return electrode connected to the patient. A plurality of electrical conductors are connected at one end to the auxiliary electrode. An opposite end of each of these conductors is electrically connected to each instrument used by the surgical personnel, with the exception of the insulated active electrode. If a metal cannula is used in conjunction with the active electrode, an electrical conductor is connected between the metal cannula and the auxiliary electrode. The auxiliary electrode and these connections establish electrical reference potential between the instruments (and any metal cannulas) and the patient, and cause any current which is unintentionally coupled to those instruments or cannulas to be harmlessly discharged through the auxiliary electrode. The auxiliary electrode has a size sufficient to conduct any unintended current into the patient without risk of an unintended burn. Additionally, because the cannulas and instruments are referenced to the potential of the patient, the risk of an unintentional current path through the surgical personnel is substantially avoided. Furthermore, the present invention also minimizes the potential for the electrosurgical voltage to create interference within a sensitive laparoscopic instrument such as a laparoscope which incorporates video circuitry within its housing.

The auxiliary electrode is separate from the primary return electrode and is not connected to the electrosurgical generator. The auxiliary electrode thus does not interfere with the operation of a contact quality monitor which monitors the integrity of the contact between the patient and a split or dual-contact primary return electrode.

The auxiliary electrode and the electrical conductors are preferably manufactured as sterile components that may be disposed of following each minimally invasive electrosurgical procedure. The auxiliary electrode and the electrical conductors are preferably packaged in separate sterile packages since it will not be known in advance how many separate conductors may be required for a particular surgical procedure. To facilitate the attachment of a plurality of instruments to the auxiliary electrode, each electrical conductor attached to an instrument is separately connected in a multi-connector electrical junction or connector block which, in turn, is connected to the auxiliary electrode.

Another aspect of the present invention relates to a method of referencing each non-insulated surgical instrument to the electrical potential of the patient during a minimally invasive electrosurgical procedure. The method includes attaching the auxiliary electrode to the patient separately from the primary return electrode. An electrical conductor is then attached between the auxiliary electrode and each surgical instrument to reference the instruments to the patient and cause any current which is unintentionally coupled to those instruments to be harmlessly discharged through the auxiliary electrode. The method of the present invention also preferably utilizes plastic or non-conducting cannulas to electrically insulate the instruments from the patient's abdominal wall. However, if metal cannulas are used in place of plastic cannulas, the method of the present invention also includes the step of connecting electrical conductors between the metal cannulas and the auxiliary electrode. In particular, an electrical conductor is connected to any metal cannula that is used in conjunction with the active surgical electrode since such a metal cannula may be energized by either a failure in the insulation of the active electrode or through capacitive coupling with the electrode.

The method further includes utilizing a contact quality monitor and a split or dual-contact primary return electrode to monitor the integrity of the contact between the patient and the primary return electrode. The separate nature of the auxiliary electrode allows for the simultaneous operation of the auxiliary electrode and the contact quality monitor.

A more complete appreciation of the present invention and its scope may be obtained from the accompanying drawings, which are briefly summarized below, from the following detail descriptions of presently preferred embodiments of the invention, and from the appended claims.

DETAILED DESCRIPTION

Figure 1:
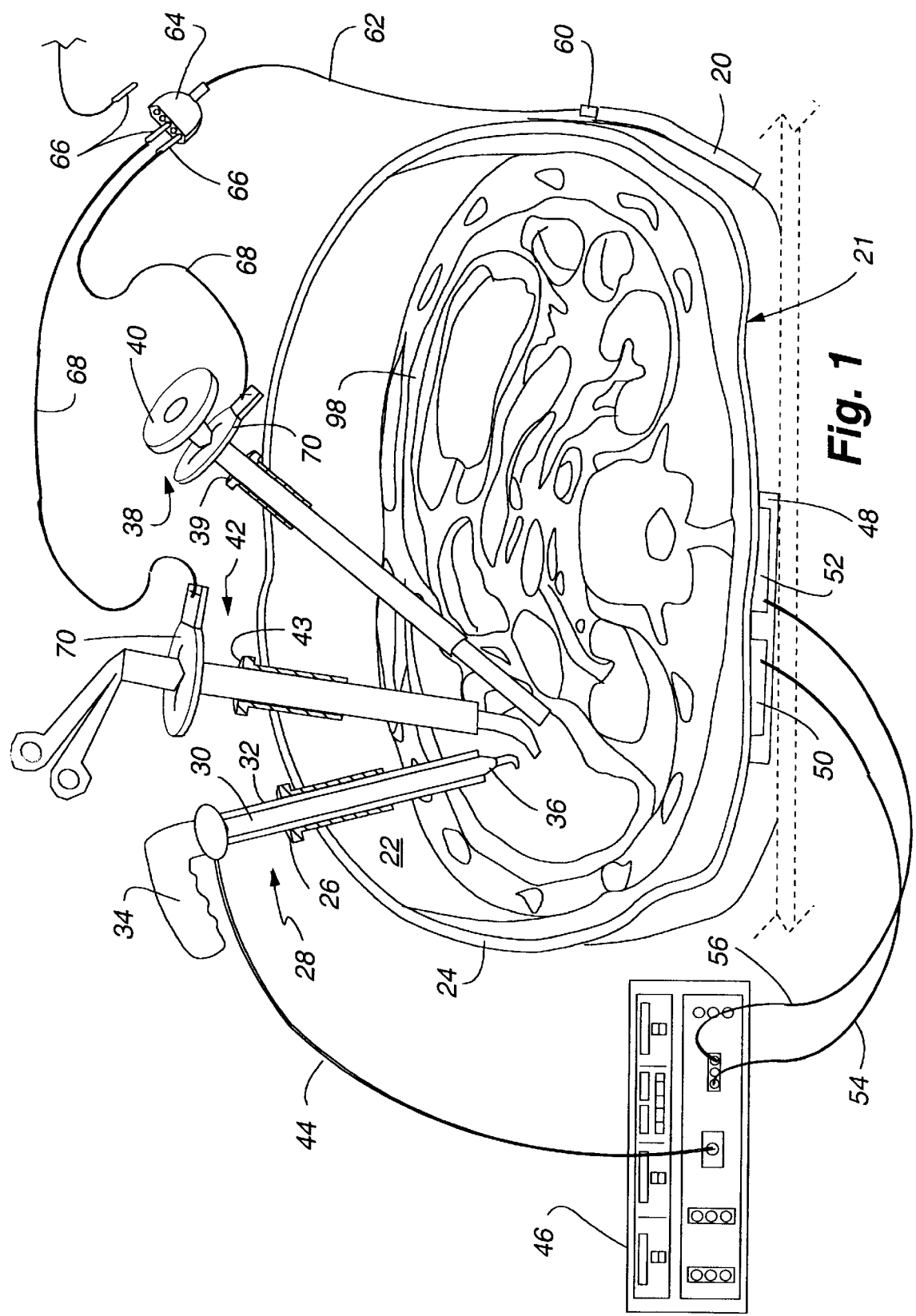
FIG. 1 is a schematic and isometric illustration showing an auxiliary electrode and connectors of the present invention connected to other surgical equipment used in a minimally invasive surgical procedure in an abdominal cavity.
Figure 2:
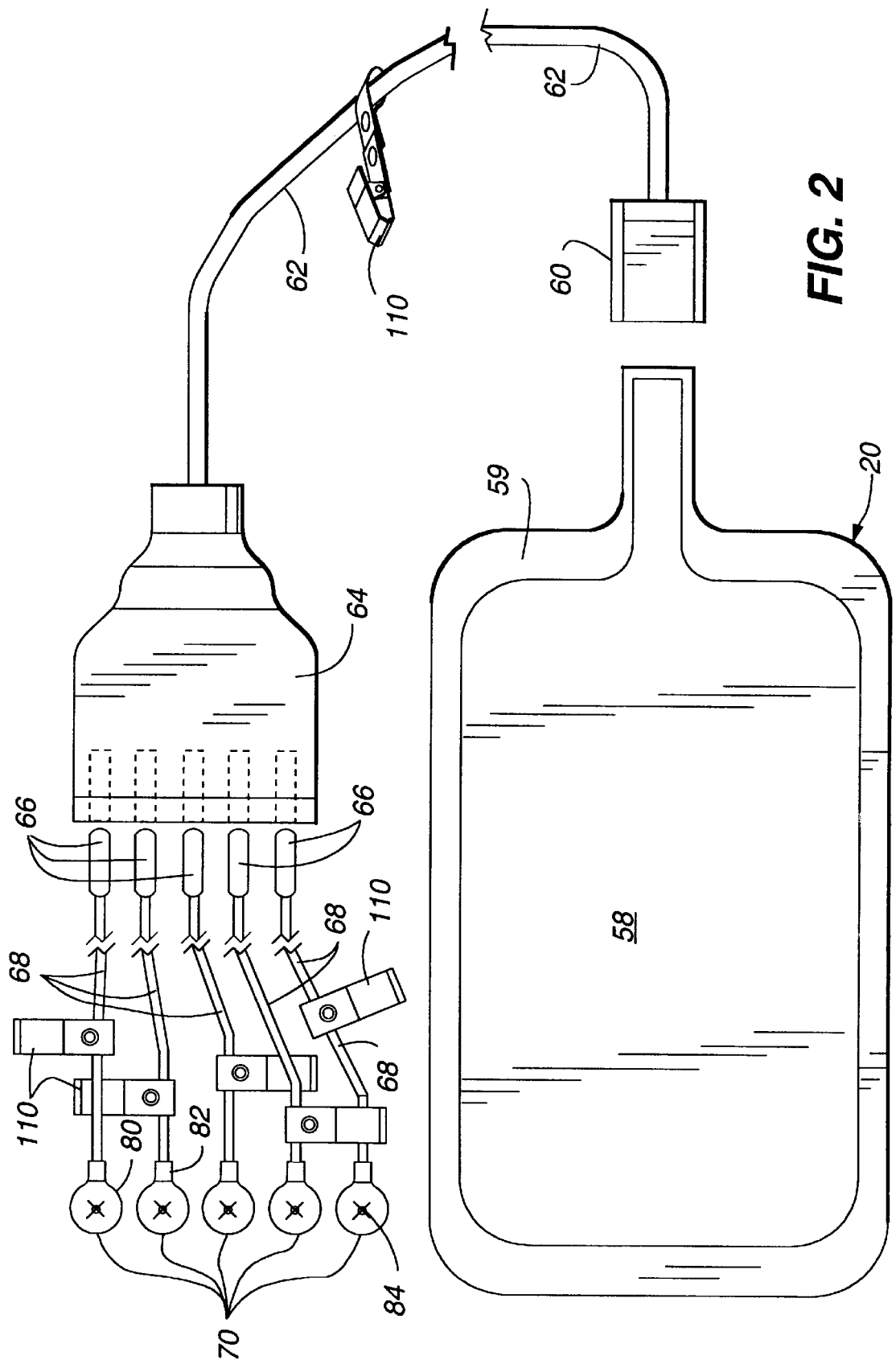
FIG. 2 is an enlarged plan view of the auxiliary electrode shown in FIG. 1 together with its associated components including five conductive instrument connectors.

The present invention includes a laparoscopic auxiliary electrode 20, shown in FIGS. 1 and 2. The auxiliary electrode 20 is shown attached to a patient 21 in FIG. 1 as it would typically be used in a minimally invasive electrosurgical procedure in an abdominal cavity 22. The auxiliary electrode 20 is connected to various surgical instruments and equipment used in the minimally invasive procedure.

A minimally invasive electrosurgical procedure typically utilizes a plurality of cannulas to provide access through an abdominal wall 24 for a number of different laparoscopic surgical instruments. Specifically, for electrosurgical procedures, one cannula 26 provides access for an electrosurgical probe 28 having an active electrode 30 for applying both cutting and coagulation high frequency waveforms to tissue of the patient 21. The electrosurgical probe 28 typically includes a layer of insulation 32 (FIG. 1) surrounding the electrode 30. A handle 34 allows a surgeon to manipulate an electrode tip 36 at a distal end of the electrosurgical probe 28. The surgical site may be visualized through a laparoscope 38 which is inserted into the abdominal cavity 22 through a second cannula 39. The laparoscope includes a light source (not shown) and an eyepiece 40 at a proximal end thereof, or alternatively, the laparoscope may comprise a video camera (not shown) which supplies electrical image signals to a video monitor (not shown) positioned within the operating theater for viewing by the surgeon. Additionally, a mechanical laparoscopic probe such as a grasper 42 may be inserted through a third cannula 43, as shown in FIG. 1, to assist in manipulating or holding tissue at the surgical site. The grasper 42 is used to hold or separate body tissue so that it may be severed or coagulated by the application of high frequency current from the electrode tip 36, or so that the tissue may be acted on with other mechanical laparoscopic surgical instruments. The light source of the laparoscope 38 illuminates the interior tissues and organs at the surgical site so that the surgeon can see the effects obtained by manipulating the probes 28 and 42 to achieve a desired surgical effect. Details of the cannulas and the laparoscopic surgical instruments are well known to those skilled in the art.

Although three cannulas 26, 39 and 43 are shown in FIG. 1, those skilled in the art will appreciate that more or fewer cannulas and surgical instruments may be used as required for a procedure. For example, if not combined with one of the other laparoscopic instruments, a separate irrigation/aspiration handpiece (not shown) may be used. Additionally, an insufflation pump and a pressure valve (neither shown) may require a separate cannula to maintain pressurized gas within the abdominal cavity 22 and distend the abdominal wall 24 as shown in FIG. 1.

The electrosurgical probe 28 is connected by a wire lead 44 to an electrosurgical generator 46 (FIG. 1). The generator 46 may typically be activated, in either a cutting, coagulation or combined mode, by depressing a switch (not shown) on the handle 34 of the probe 28 or by depressing a separate foot switch (not shown). When the surgeon activates the generator 46, the high frequency current is sent through the wire lead 44 to the tip 36 of the active electrode 30. The current creates the desired electrosurgical effect on the tissue at the location of the tip 36 and then passes harmlessly through the patient 21 and is returned to the electrosurgical generator 46 through a primary return electrode 48 which is typically fixed to the patient.

The primary return electrode 48 is preferably a split or dual-foil electrode having two separate patient contacts 50 and 52 which are separated from one another. The size of the two separate patient contacts 50 and 52 ensure that the current passing from the patient 21 to the primary return electrode 48 in the return path back to the electrosurgical generator 46 will not burn the patient at the site where the return electrode 48 is attached. However, if the contacts 50 and 52 should become partially detached from the patient, so that the current density through the remaining connected portions of the contacts 50 and 52 increases, the possibility of burning the patient unintentionally at a location other than the surgical site during activation of the generator 46 is increased.

To help prevent burns arising from reduced surface contact between the patient and the primary return electrode 48, the electrosurgical generator 46 preferably includes a conventional return electrode contact quality monitor. In normal operation, the primary return electrode 48 returns electrosurgical current from both patient contacts 50 and 52 along separate wire leads 54 and 56, respectively. However, the contact quality monitor sends an additional signal between the two patient contacts 50 and 52 via the separate wire leads 54 and 56, and measures the resistance or impedance of the patient tissue between the two contacts 50 and 52 by evaluating the characteristics of the signal. When the contact quality monitor determines that the resistance between the two contacts has increased to an unacceptable level, the generator 46 is disabled. Such an increase in the resistance between the patient contacts 50 and 52 is an indication that at least one of the contacts has become detached from the patient to an extent that the current density is approaching a level that could burn the patient. The contact quality monitor thus acts to prevent such burns by disabling the generator 46 and allowing the surgical personnel to reattach the patient contacts of the primary return electrode 48.

The auxiliary electrode 20 of the present invention works separately from and in conjunction with the primary return electrode 48 and the contact quality monitor to help eliminate the potential for unintentional burns during electrosurgery, while not interfering with the function of the primary return electrode 48 or the contact quality monitor. The auxiliary electrode 20 acts to reference laparoscopic surgical instruments to the potential of the patient, as shown in FIG. 1, thereby preventing the laparoscopic instruments from obtaining a sufficient potential with respect to the patient 21 to unintentionally harm the patient or the attending surgical personnel.

Figure 10:
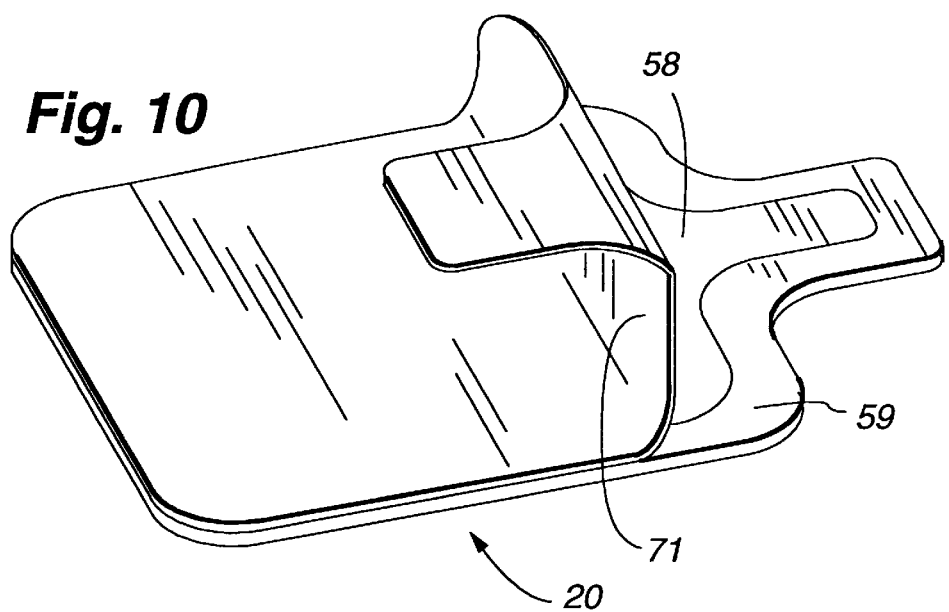
FIG. 10 is an isometric view of the auxiliary electrode shown in FIG. 1, illustrating a sterile backing used to package the auxiliary electrode.

The auxiliary electrode 20, shown in FIGS. 2 and 10, is preferably a single foil patient contact 58 which provides contact with the patient's skin over a relatively large surface area compared to the contact area of a 35 cannula. However, the surface area of the auxiliary electrode 20 is preferably smaller than the surface area of the two patient contacts 50 and 52 which make up the primary return electrode 48, since the auxiliary electrode should not normally carry current. For example, the size of the auxiliary electrode 20 is similar to that of a pediatric ground pad. An adhesive marginal area 59 (FIG. 10) attaches the auxiliary electrode to the patient. A conductive gel (not shown) covers the contact 58 to enhance the electrical connection to the patient 21. In general, the construction of the auxiliary electrode 20 is conventional and typical of return electrodes.

An auxiliary electrode connector 60 (FIG. 2) is releasably attached to one end of the auxiliary electrode 20 to make electrical contact with the contact 58. An insulated cable 62 attaches the connector 60 to a conventional multi-port connector, such as a multi-port, R-type junction block 64. The R-type junction block 64 preferably accommodates up to five connectors 66, such as R-connectors. Each connector 66 is attached to an insulated electrical lead 68 which, in turn, is attached at its opposite end to a conductive instrument connector 70. The instrument connector 70 is then attached to any laparoscopic instrument or conductive cannula which may be susceptible to an unintentional electrical charge, e.g., the grasper 42 or the laparoscope 38 shown in FIG. 1.

Once the auxiliary electrode 20 is attached to the patient, the electrode connector 60 is attached to the auxiliary electrode 20, the individual conductive instrument connectors 70 are attached to different laparoscopic instruments, and the connectors 66 are plugged into the junction block 64, as shown in FIG. 1. Once connected in this manner, the attached laparoscopic instruments will be referenced to the potential of the patient. Thus, should the active electrode 30 accidentally contact one of the referenced instruments such as the grasper 42 (FIG. 1), the high frequency energy from the electrosurgical generator 46 will be conducted through the instrument connector 70, the instrument lead 68, the unction block 64, the insulated cable 62 and the connector 60 to the auxiliary electrode 20 where the energy is safely dispersed into the patient 21 over the relatively large surface area of the auxiliary electrode 20. The current is then returned from the patient at the primary return electrode 48 to the electrosurgical generator 46 (FIG. 1).

Figure 11:
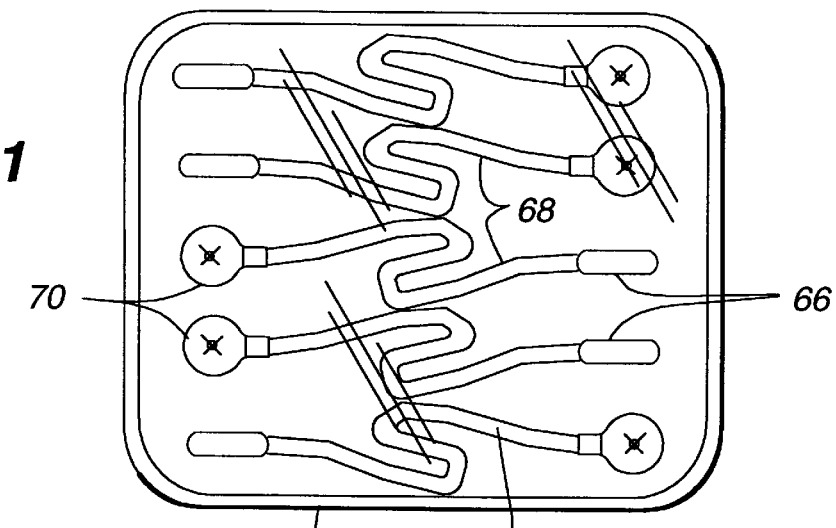
FIG. 11 is a plan view of five instrument connectors shown in FIG. 2, illustrating the instrument connectors packaged in a sterile pouch.
Figure 12:
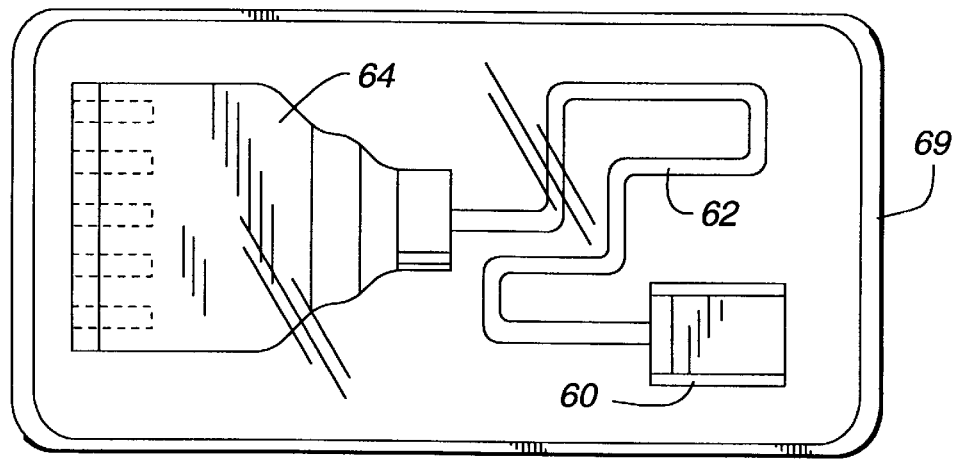
FIG. 12 is a plan view of an electrical junction block shown in FIGS. 1 and 2, illustrating the junction block packaged in a sterile pouch.

The auxiliary electrode 20, as well as the instrument connector 70 and its attached instrument lead 68 and connector 66, are preferably manufactured as separately-packaged sterile components, which may be disposed of following each surgical procedure. For example, FIG. 11 illustrates five instrument connectors 70 and their attached leads 68 and connectors 66 enclosed within a sterile pouch 69 having a clear plastic cover. Additionally, the junction block 64 and its insulated cable 62 and electrode connector 60 may be manufactured as a separately-packaged sterile and disposable component, although it is preferred that the junction block 64 and the cable 62 be manufactured as a reusable component that may be sterilized between surgical procedures. FIG. 12 illustrates a disposable embodiment of the junction block 64 also packaged in a sterile pouch 69 with a clear plastic cover. Alternatively, if the junction block 64 is manufactured as a disposable component, the junction block cable 62 may be directly and permanently connected (not shown) to the disposable auxiliary electrode 20, thereby obviating the need for a separate electrode connector 60. Additionally, FIG. 10 illustrates a sterile backing 71 attached to the adhesive marginal area 59 of the auxiliary electrode 20. The sterile backing 71 covers the adhesive gel (not shown) on the patient contact 58 until the auxiliary electrode 20 is attached to a patient 21.

Figure 3:
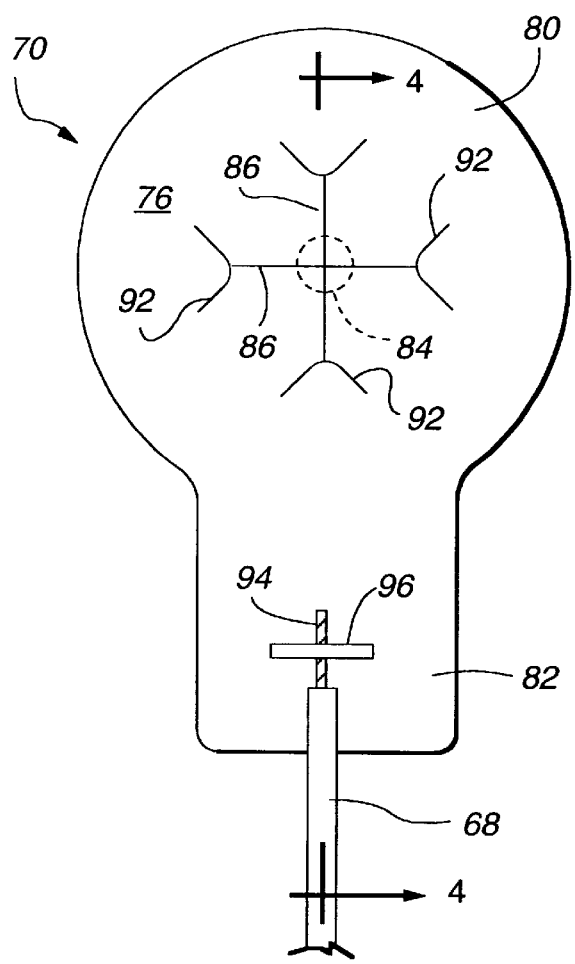
FIG. 3 is an enlarged plan view of one of the conductive instrument connectors shown in FIGS. 1 and 2.
Figure 4:
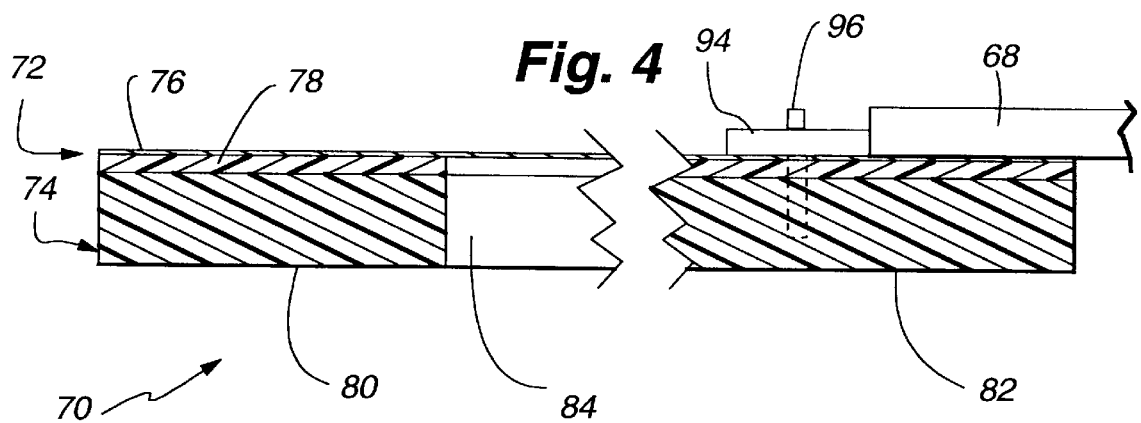
FIG. 4 is a cross-section view taken substantially in the plane of line 4—4 of FIG. 3.

The conductive instrument connector 70, shown in detail in FIGS. 3 and 4, is preferably formed as a laminate having a relatively thin and flexible top layer 72 fixed to a relatively thick, resilient bottom layer 74 by an adhesive (not shown). The top layer 72 includes a thin layer of conductive foil 76 (FIG. 4) deposited on a carrier 78 preferably made from Mylar®. The Mylar® carrier 78 allows the foil layer 76 to be processed without damaging the conductive foil. The top layer 72 preferably has a thickness of approximately two mils, while the relatively thick bottom layer 74 preferably has a thickness of approximately ten mils. The bottom layer 74, also preferably made from Mylar®, forms the body of the instrument connector 70 and provides a resilient spring character discussed in greater detail below. The top and bottom layers 72 and 74 are laminated together with an adhesive (not shown).

Figure 5:
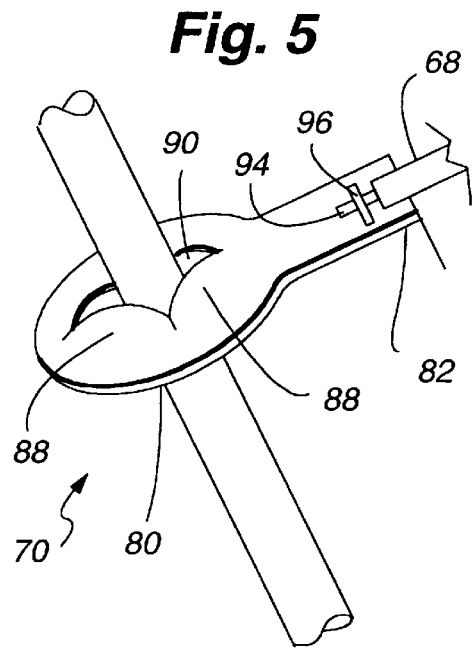
FIG. 5 is an enlarged isometric view illustrating the attachment of a conductive instrument connector to a surgical instrument as shown in FIG. 1.

The instrument connector 70 includes a substantially rounded end portion 80 with a tapered arm portion 82 extending away from the rounded end portion 80. Cuts are formed in the rounded end portion 80 as shown in FIG. 3, with each cut extending through both the top and bottom layers 72 and 74 of the laminated instrument connector 70. A circular cut 84 is made at the center of the rounded end portion 80, and four identical lateral cuts 86 extend outward from the circular cut 84 at 90 degree intervals to form four perpendicular angles. Four flaps 88 are defined by the material between the four lateral cuts 86 and the circular cut 84. The four flaps 88 are folded downward to form an instrument channel 90 through the instrument connector 70 when the distal end of a laparoscopic instrument is inserted from the top layer 72 to the bottom layer 74 (FIG. 5). Depending on the size of the outer diameter of the laparoscopic instrument, the flaps 88 are bent an appropriate degree to accommodate the width of the instrument. Chevron-shaped cuts 92 at the outer ends of the four lateral cuts 86 terminate the lateral cuts 86 and provide a maximum size for the instrument channel 90. The maximum size of the instrument channel 90 (i.e., the distance between the closed ends of opposing chevron cuts 92) is preferably sufficient to accommodate the largest laparoscopic instruments or cannulas currently used. For example, since 11 millimeter cannulas are currently the largest laparoscopic instruments that are used during minimally invasive surgery, the distance between the closed ends of the opposing chevron cuts 92 would preferably be approximately 11 millimeters.

The resilient spring nature of the Mylar® bottom layer 74 and the Mylar® backing on the top layer 72 of the instrument connector 70 maintains the flaps 88 in firm engaging contact with the outer surface of any laparoscopic instrument inserted through the instrument channel 90 (FIG. 5). Therefore, even after the flaps 88 have been bent downward by insertion of the instrument through the channel 90 as shown in FIG. 5, the spring nature of the flaps 88 will retain the instrument connector 70 in a desired position on the instrument and will ensure that the conductive foil 76 on the top layer 72 maintains an effective electrical contact over a significant surface of the metal instrument. Furthermore, the resiliency of the flaps 88 assure that they conform to a significant portion of the outer surface of a variety of different shaped surgical instruments. If the instrument connector 70 is used with a surgical probe or laparoscope as shown in FIGS. 1 and 5, the connector 70 need only be slid over the length of the instrument from its distal end so that the instrument can then be inserted through a cannula and into the abdominal cavity 22.

FIGS. 3–5 further show the connection of the instrument lead 68 to the instrument connector 70. One end 94 of the insulated instrument lead 68 is stripped of insulation to expose the bare wire. The stripped end 94 is then permanently attached to the conductive foil 76 on the tapered arm portion 82 of the instrument connector 70 by a conductive staple 96. The staple 96 is preferably made from brass to provide a substantial connection between the stripped end 94 of the instrument lead 68 and the foil surface of the instrument connector 70. In use, the instrument connector 70 and the connected instrument lead 68 are attached to an instrument as shown in FIGS. 1 and 5. The connector 66 at the opposite end of the instrument lead 68 is attached to the junction block 64 which, in turn, is connected to the auxiliary electrode 20 via the insulated cable 62 and the electrode connector 60. At that point, the surgical instrument is referenced to the potential of the patient and any unintentional current applied to the instrument will be conducted to the auxiliary electrode 20 where it will be safely dispersed over the entire surface area of the auxiliary electrode 20 and into the patient 21.

The present invention is preferably used in conjunction with non-conducting (i.e., plastic) cannulas to prevent unintentional energization of the cannulas during the laparoscopic procedure. Thus, the cannulas 26, 39 and 43 illustrated in FIG. 1 are preferably plastic cannulas. The use of plastic cannulas is in direct opposition to the recent recommendations that only metal cannulas be used in laparoscopic procedures so any current accidentally applied to a metal cannula or its associated laparoscopic instrument would be directed to the return electrode through the patient's abdominal wall. This recommendation followed from the belief that there was a sufficiently large surface area interface between the conductive cannula and the patient's abdominal wall to provide a safe path for the electrical current and thereby prevent unintentional patient burns. However, it has been discovered that the energization of conductive cannulas may indeed cause a burn at the cannula insertion site within the abdominal wall.

For example, with an electrosurgical generator set to deliver a 35 watt coagulation waveform, and where the impedance between a 5 millimeter metal cannula and the patient's abdominal wall is a nominal value of 200 ohms, approximately 29 watts would be delivered to the patient's abdominal wall, as determined from analyzing the load regulation curves typically found in the generator operating manual. Solving the equation $P=I^2 \times R$ for the current value I, it can be seen that approximately 381 milliamps will be delivered to the patient's abdominal wall under these circumstances. An analysis of tissue temperature rise shows that an application of such a 381 milliamp current will raise the insertion site tissue temperature to 55 degrees Celsius within ten seconds. Such a temperature rise virtually ensures a burn in the abdominal wall at the cannula insertion site.

Thus, the use of plastic cannulas with the present invention helps to ensure that any current unintentionally applied to an instrument within the abdominal cavity (such as the laparoscope 38 or the grasper 42 shown in FIG. 1) will be dispersed through the auxiliary electrode 20 rather than through the patient's abdominal wall, or through unintentional contact of the distal end of the cannula with an internal organ, thereby preventing unintentional burns to the abdominal wall. Additionally, because plastic cannulas can not be energized by direct contact with the electrode tip 36, the failure of the electrode insulation 32 within the cannula or by capacitive coupling with the electrode 30, the distal ends of plastic cannulas can not cause unintentional burns to the patient's other internal organs such as the bowel 98. Therefore, when the present invention is used with plastic cannulas, instrument connectors 70 need only be applied to the laparoscope 38, the grasper 42 and any other inserted instruments to prevent patient burns should the active electrode tip 36 accidentally contact one of these instruments during the surgical procedure. The present invention does not rely on the conductivity of the cannulas.

Figure 9:
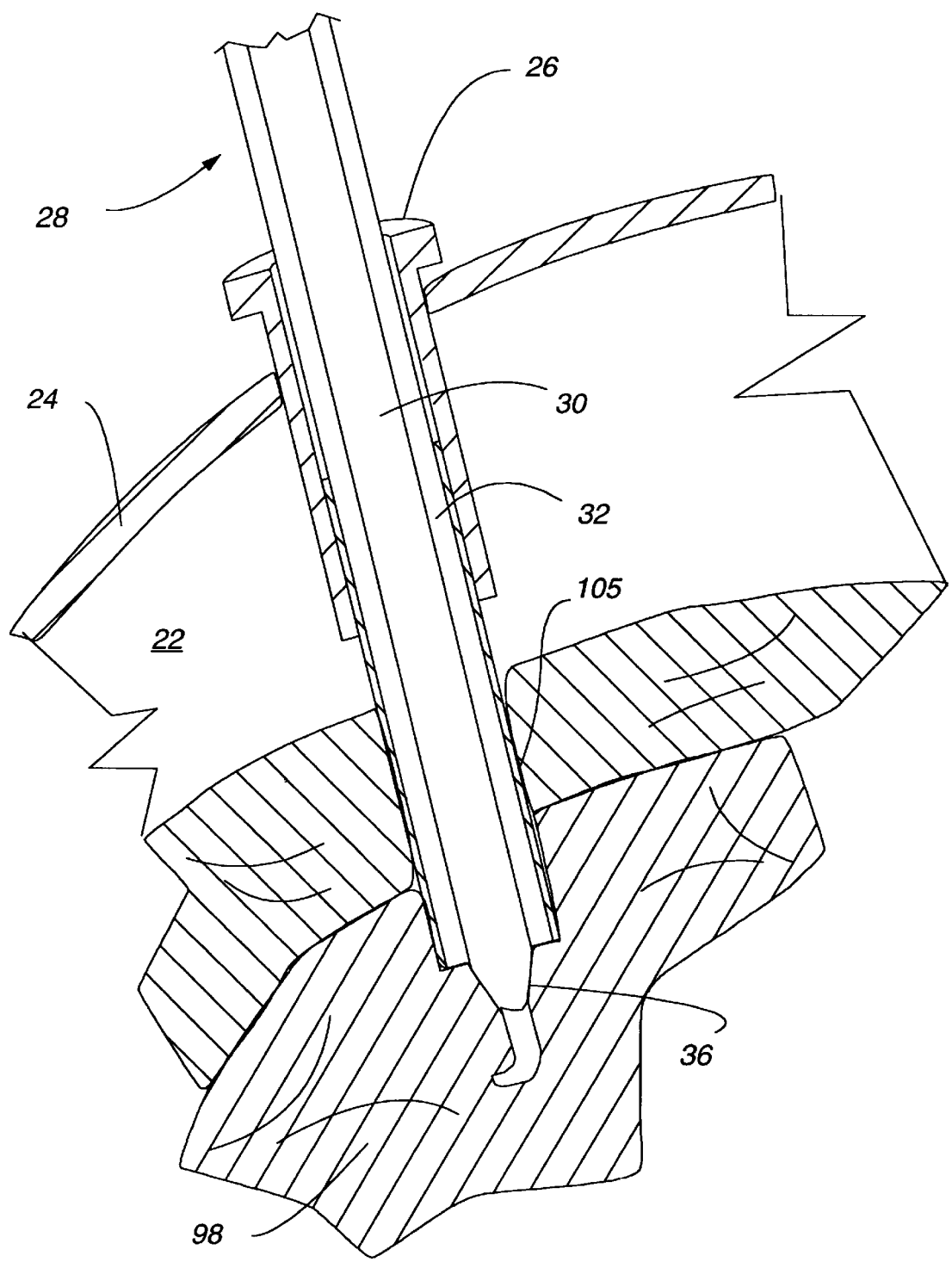
FIG. 9 is a partial enlarged schematic and isometric illustration showing a supplemental insulation sleeve attached to a distal end of an active electrode shown in FIG. 1.

The only scenario in which the combination of the auxiliary electrode and the plastic cannulas will not prevent unintentional patient burns is where the electrode insulation 32 fails at a point beyond the distal end of the plastic cannula 26. However, current leakage resulting from an insulation defect outside of the plastic cannula 26 could be eliminated by the use of supplemental insulation sleeves which can be applied over the distal end of the electrosurgical probe 28. An example of such an insulating sleeve 105 is shown in FIG. 9, where the sleeve 105 extends over the distal portion of the probe 28 from a position adjacent the distal end of the plastic cannula 26 to a position adjacent the active electrode tip 36. The thickness of the sleeve 105 must be sufficient to prevent current leakage should the electrode insulation 32 fail, but must be thin enough to allow the distal end of the probe 28 to fit through the cannula 26. The sleeve 105 is manufactured as a sterile component that is disposed of following the surgical procedure, and is preferably made from silicone to withstand the high temperatures near the electrode tip 36.

Figure 6:
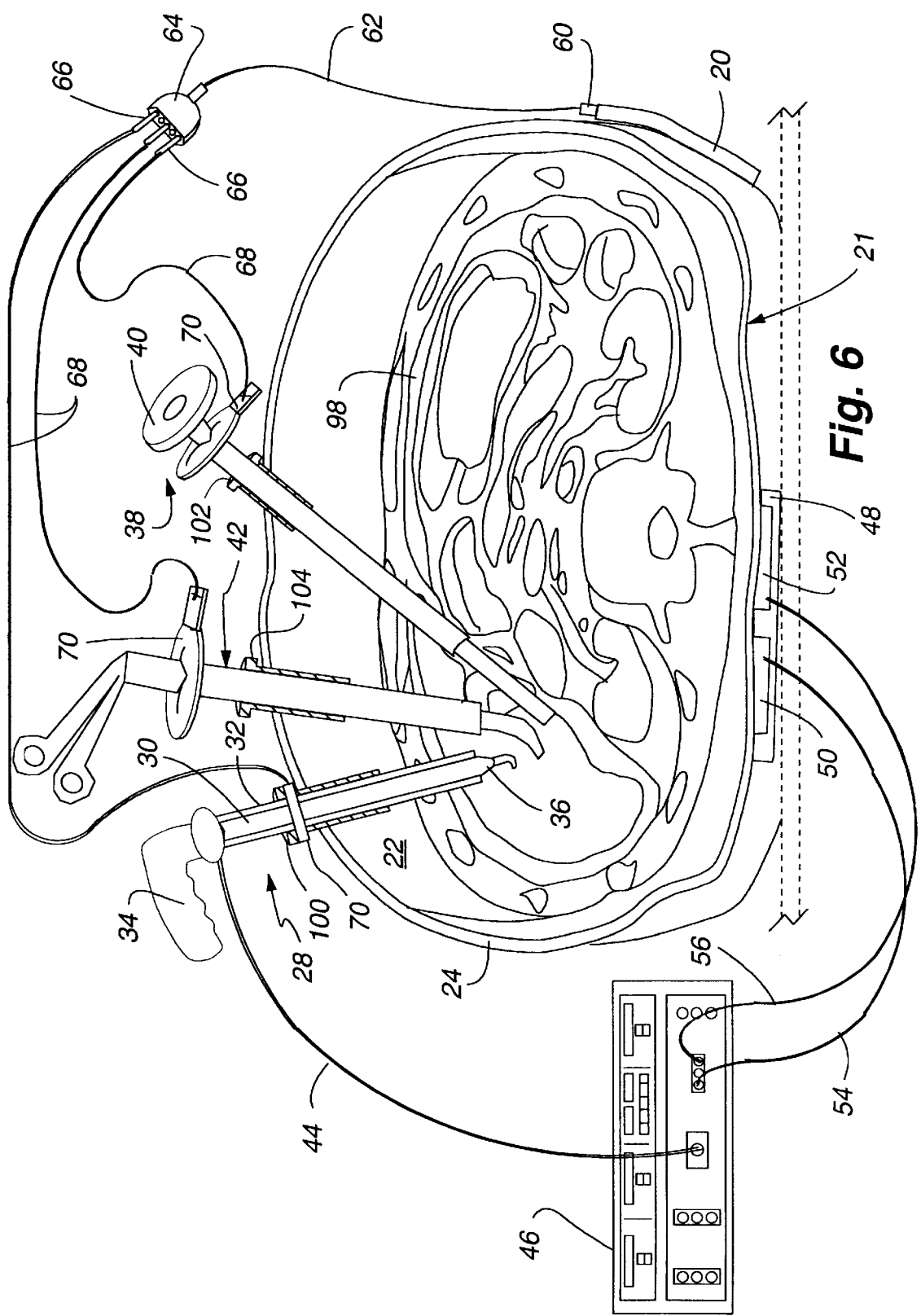
FIG. 6 is an schematic and isometric view similar to FIG. 1 illustrating the attachment of an additional conductive instrument connector to a metal cannula within which an active electrosurgical probe is inserted.

The present invention is also used effectively with metal cannulas. FIG. 6 shows metal cannulas 100, 102 and 104 used in place of the plastic cannulas 26, 39 and 43 (FIG. 1) for the electrosurgical probe 28, the laparoscope 38 and the grasper 42, respectively. In this instance, a separate instrument connector 70 is connected to the metal cannula 100, preferably by applying it over the distal end of the metal cannula 100 before the cannula is inserted through the incision in the abdominal wall 24. The outer diameter of the distal end of the metal cannula 100 is substantially the same as the outer diameter of the probe 28 so that the preferred embodiment of the instrument connector 70 will fit over the metal cannula substantially as described above with respect to the laparoscopic instrument illustrated in FIG. 5. However, a larger rounded end portion 80 and larger flaps 88 of the instrument connector 70 may be provided if necessary to accommodate the metal cannula. Once the metal cannula 100 is attached to the auxiliary electrode 20 in this manner, any current applied to the metal cannula 100 (such as by capacitive coupling with the electrode 30, current leakage through the insulation 32 at a point within the cannula 100, or unintentional contact of the active electrode with the cannula) will be safely dispersed as described above. Separate instrument connectors 70 are not shown attached to the metal cannulas 102 and 104 in FIG. 6 because any current applied directly to these cannulas is channeled through their respective instruments and to the attached instrument connectors 70. However, in the interest of redundancy, it is within the scope of the present invention to attach additional instrument connectors 70 (not shown) to the cannulas 102 and 104 as was done with respect to the cannula 100 in FIG. 6. Furthermore, it is also within the scope of the present invention to attach instrument connectors 70 only to the metal cannulas as opposed to their respective instruments, although it is preferred to connect the instruments directly to the auxiliary electrode 20 as shown in FIG. 6 since the instruments themselves are more likely than their respective metal cannulas to be energized by direct contact with the active electrode tip 36.

A separate instrument connector 70 is not placed about the electrosurgical probe 28 due to the danger of grounding out the active electrode 30 or producing an unnecessary source for capacitive coupling with the active electrode 30. However, in some cases a multi-function laparoscopic handpiece (not shown) may be used in place of the probe 28. An example of such a handpiece is shown in U.S. Pat. No. 5,449,356, entitled MULTIFUNCTIONAL PROBE FOR MINIMALLY INVASIVE SURGERY, in which a single housing may contain a standard blade electrode together with a nozzle and electrode assembly for gas-assisted fulguration and a means for either irrigation or aspiration. If such a multifunctional probe were used in the place of the standard electrosurgical probe 28, a separate conductive instrument connector 70 may be attached to the multifunctional probe to prevent accidental burns from either a breakdown in electrode shielding within the multifunctional probe or from capacitive coupling between the electrode and other metal components within the multifunctional probe.

Although a preferred embodiment of the instrument connector 70 has been described above in association with FIGS. 1–6, it should be understood that the present invention encompasses any type of electrically conductive connector that will remain attached to a laparoscopic instrument or cannula during a minimally invasive surgical procedure. The preferred instrument connector 70 has many advantages including its ability to be quickly and easily placed over the distal end of a laparoscopic instrument and positioned as desired by the surgeon. Additionally, the preferred instrument connector 70 may be easily rotated about the attached instrument while maintaining its longitudinal position on the instrument. This ability to rotate the preferred instrument connector 70 is important to prevent the instrument lead 68 attached to the tapered arm portion 82 of the connector from being wound about the instrument should the instrument need to be frequently rotated within its cannula during the course of the laparoscopic procedure. For instance, the grasper 42 may need to be rotated about its longitudinal axis numerous times over the course of the procedure. By rotating the tapered arm portion 82 of the instrument connector 70 as the grasper 42 is rotated, the instrument lead 68 will not be wound about the grasper, thereby avoiding the potential situation of shortening the length of the instrument lead 68 to the point where it is pulled taught between the grasper and the junction block 64.

Figure 7:
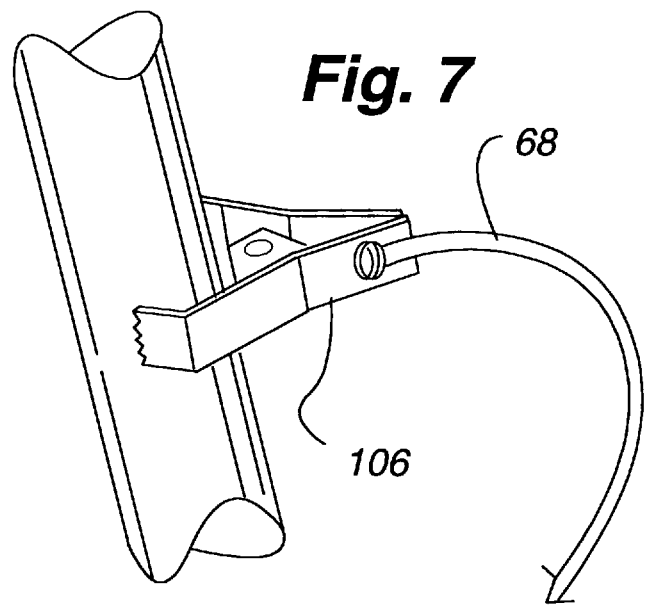
FIG. 7 is an isometric view showing the attachment of a first alternative conductive instrument connector to a laparoscopic instrument.
Figure 8:
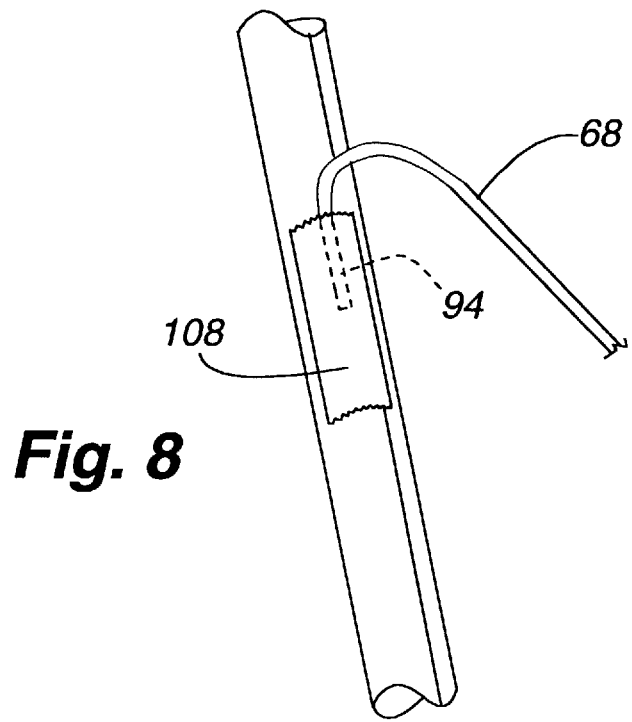
FIG. 8 is an isometric view showing the attachment of a second alternative conductive instrument connector to a laparoscopic instrument.

While the preferred instrument connector 70 provides a number of advantages, it is recognized that other types of conductive connectors may be effectively used with the auxiliary electrode 20. For example, FIG. 7 illustrates a known metal crocodile or alligator clip 106 connecting a laparoscopic instrument to the auxiliary electrode 20 via the attached instrument lead 68. The clip 106 may easily be connected and disconnected from the instrument and may additionally be rotated about the instrument as the instrument is rotated about its longitudinal axis within the cannula. Additionally, FIG. 8 illustrates a piece of conductive tape 108 holding the stripped end 94 of the instrument lead 68 to the laparoscopic instrument in a known manner. The conductive tape 108 is less convenient than either the preferred connector 70 or the clip 108 since it may not be easily rotated about the outer diameter of the instrument, but the tape 108 represents a low cost connector for attaching the instrument lead 68 to the instrument. A wide variety of other devices and techniques exist for attaching a laparoscopic instrument to the auxiliary electrode 20, and it is understood that the present invention is not limited by the disclosure of the preferred embodiment of the instrument connector 70.

Although prior art laparoscopic surgical instruments have provided a means for connecting the instrument directly to the electrosurgical generator to prevent surgical personnel from being shocked or burned when the instrument is unintentionally energized, the auxiliary electrode of the present invention provides many advantages over such prior art techniques. First, the provision of a completely separate patient ground pad allows the auxiliary electrode to be characterized as a distinct secondary system which does not interfere with or complicate the use of the primary electrosurgical system consisting of the electrode 30, the electrosurgical generator 46 and the primary return electrode 48. The separate and distinct nature of the auxiliary electrode 20 is significant in that the auxiliary electrode will not interfere with the important operation of the contact quality monitor. Because the auxiliary electrode 20 is not connected directly to the primary return electrode 48, the impedance measuring signals transmitted between the contact quality monitor and the two patient contacts 50 and 52 of the primary return electrode will not be affected by the operation of the auxiliary electrode 20.

A further advantage over prior art instruments having their own ground wire connected to an electrosurgical generator is that the auxiliary electrode 20 may be connected to a number of different laparoscopic instruments (e.g., up to five instruments via the junction block 64 illustrated in FIG. 1), while prior art electrosurgical generators could typically be modified to connect only one instrument (usually a colonoscope). Additionally, use of the auxiliary electrode 20 requires no modifications to the electrosurgical generator (as opposed to other prior art surgical instruments which do not include a separate connector or ground pad), thereby allowing the auxiliary electrode to be used with any available generator. Furthermore, by running the instrument leads 68 directly from the laparoscopic instruments to the auxiliary electrode 20 (via the junction block 64), no additional wires extend between the patient and the electrosurgical generator. This is an important consideration, particularly in those instances where a large number of laparoscopic instruments are used, since each additional wire between the patient and the generator interferes with movement of surgical personnel and equipment in the operating room. Precise placement of the instrument leads 68 (as well as the insulated connector cable 62 leading from the junction block 64) on the patient may be obtained by the use of conventional positioning clips 110 to attach the wires to a portion of a sheet or sterile drape away from the surgical site. In this manner, the auxiliary electrode and its associated components can be positioned away from the remainder of the laparoscopic instruments and substantially out of sight of the surgical personnel. Additionally, the instrument leads 68 are preferably formed of sufficient length to allow the attached surgical instrument to be removed from and reinserted within the cannula during the surgical procedure should a different instrument (with its own attached instrument connector 70 and instrument lead 68) need to be inserted within the cannula. Lastly, the auxiliary electrode and a majority of its associated components are preferably manufactured as disposable items to simplify both setting up and disassembling the auxiliary electrode 20.

Presently preferred embodiments of the invention and many of their improved aspects have been described with a degree of particularity. This description is preferred examples of implementing the invention, and is not necessarily intended to limit the scope of the invention which is defined by the scope of the following claims.

What is claimed is:

1. A system for connecting a plurality of non-insulated, minimally invasive surgical instruments to an auxiliary electrode attached to a patient at a first location during minimally invasive electrosurgery during which high frequency energy is normally transferred from an electrosurgical generator to an active electrode extending into a patient cavity and applied at a surgical site within the patient cavity, said high frequency energy returning to the electrosurgical generator through a primary return electrode attached to the patient at a second location separated from the first location of the auxiliary electrode, said system comprising:

a plurality of instrument connectors, each instrument connector having a conductive surface adapted to be releasably connected to one of the plurality of non-insulated surgical instruments at a location outside the patient cavity;

a plurality of instrument leads, each instrument lead attached at a first end to the conductive surface of one of the instrument connectors; and a junction block by which to electrically connect opposite ends of the plurality of the instrument leads to the auxiliary electrode to electrically reference each said non-insulated surgical instrument to the electrical potential of the patient through the auxiliary electrode; and wherein each instrument connector further comprises:

a rounded end portion defining a channel for insertion of one of the non-insulated surgical instruments; and a tapered end portion attached to the rounded end portion, said tapered end portion attached to the first end of one of the instrument leads.

2. A system as defined in claim 1, further comprising:

a plastic cannula adapted to be inserted through a patient wall to provide a guide for insertion of the non-insulated surgical instrument into the patient cavity and to electrically insulate the patient wall from the non-insulated surgical instrument during the minimally invasive electrosurgery.

3. A system as defined in claim 1, wherein:

the rounded end portion of the instrument connector includes a plurality of cuts which define a plurality of flaps;

said flaps resiliently deflect against the surgical instrument to form the channel and establish an electrical contact with the surgical instrument.

4. A system as defined in claim 1, wherein the instrument connector further comprises a spring-biased metal clip having jaws biased to releasably grip the non-insulated surgical instrument.

5. A system as defined in claim 1, wherein the instrument connector further comprises a piece of conductive tape adapted to connect to the non-insulated surgical instrument.

6. A system as defined in claim 1, wherein the junction block further comprises:

a plurality of receptacles adapted to receive the opposite ends of the instrument leads attached to the instrument connectors;

an insulated electrical cable having first and second ends, said first end of the insulated electrical cable electrically connected to each of the receptacles; and an electrode connector connected to the second end of the insulated electrical cable, said electrode connector adapted to electrically connect the second end of the insulated electrical cable to the auxiliary electrode.

7. A system as defined in claim 6, wherein the junction block is manufactured as a disposable item for disposal following the minimally invasive electrosurgery; said system further comprising:

a sterile pouch enclosing the junction block prior to the minimally invasive electrosurgery.

8. A system as defined in claim 1, further comprising:

a sterile pouch enclosing the plurality of the disposable instrument connectors and attached instrument leads prior to the minimally invasive electrosurgery.

9. A system as defined in claim 1, wherein the conductive surface further comprises:

a layer of aluminum deposited upon a top surface of both the rounded end portion and the tapered end portion of the instrument connector.

10. A system as defined in claim 9, wherein:

the rounded end portion of the instrument connector includes a plurality of cuts which define a plurality of flaps;

a top surface of the flaps contains the deposited layer of aluminum;

the flaps are forced open by a distal end of the surgical instrument to define the channel for insertion of the instrument through the rounded end portion of the instrument connector; and a portion of the top surface of the flaps remains in contact with the surgical instrument when the distal end of the instrument is inserted through the channel from the top surface of the rounded end portion of the instrument connector.

11. A system as defined in claim 9, wherein the first end of the instrument lead is attached to the layer of aluminum deposited on the top surface of the tapered end portion of the instrument connector.

12. A system for use in preventing patient burns from a non-insulated and unintentionally charged minimally invasive surgical instrument used during minimally invasive electrosurgery during which high frequency energy is normally transferred from an electrosurgical generator to an active electrode extending into a patient cavity and applied at a surgical site within the patient cavity, said high frequency energy returning to the electrosurgical generator through a primary return electrode attached to the patient at a first location, and said electrosurgical generator including a contact quality monitor to monitor the contact between the patient and the primary return electrode, said system comprising:

an auxiliary electrode separate from the primary return electrode, said auxiliary electrode adapted to be attached to the patient at a second location separated from the first location of the primary return electrode to create an electrical reference to the patient separate from and independent of the primary return electrode;

an instrument connector having a conductive surface adapted to be releasably attached to the non-insulated surgical instrument at a location outside the patient cavity during the minimally invasive electrosurgery;

an instrument lead attached between the auxiliary electrode and the instrument connector to reference the non-insulated surgical instrument to the electrical potential of the patient through the auxiliary electrode; and said auxiliary electrode having a sufficient size to conduct any burn-producing current from the non-insulated surgical instrument into the patient to prevent burns from the non-insulated surgical instrument while simultaneously preventing the burn-producing current from interfering with operation of the contact quality monitor.

13. A system as defined in claim 12, wherein:

the instrument connector is adapted to rotate freely about the non-insulated surgical instrument while maintaining contact between the conductive surface and the non-insulated surgical instrument.

14. A system for use in preventing patient burns from a non-insulated and unintentionally charged minimally invasive surgical instrument used during minimally invasive electrosurgery during which high frequency energy is normally transferred from an electrosurgical generator to an active electrode extending into a patient cavity and applied at a surgical site within the patient cavity, said high frequency energy returning to the electrosurgical generator through a primary return electrode attached to the patient at a first location, said system comprising:

an auxiliary electrode separate from the primary return electrode, said auxiliary electrode adapted to be attached to the patient at a second location separated from the first location of the primary return electrode to create an electrical reference to the patient separate from and independent of the primary return electrode;

an instrument connector having a conductive surface adapted to be releasably attached to the non-insulated surgical instrument at a location outside the patient cavity during the minimally invasive electrosurgery;

an instrument lead attached between the auxiliary electrode and the instrument connector to reference the non-insulated surgical instrument to the electrical potential of the patient through the auxiliary electrode; and said auxiliary electrode having a sufficient size to conduct any burn-producing current from the non-insulated surgical instrument into the patient to prevent burns from the non-insulated surgical instrument while simultaneously preventing the burn-producing current from interfering with any electrical monitoring occurring at the primary return electrode.

15. A system as defined in claim 14, further comprising:
a plastic cannula adapted to be inserted through a patient wall to provide a guide for insertion of the non-insulated surgical instrument into the patient cavity and to electrically insulate the patient wall from the non-insulated surgical instrument.

16. A system as defined in claim 14, further comprising:
a metal cannula adapted to be inserted through a patient wall to provide a guide for insertion of the active electrode into the patient cavity; and
an instrument connector and instrument lead releasably attached to the metal cannula to electrically connect the metal cannula to the auxiliary electrode.

17. A system as defined in claim 14, further comprising:
an instrument lead connector fixed to one end of the instrument lead opposite the attached instrument connector; and
a junction block electrically coupled to the auxiliary electrode, said junction block adapted to receive a plurality of instrument lead connectors to electrically connect a plurality of instrument connectors to the auxiliary electrode.

18. A system as defined in claim 14, wherein the instrument connector further comprises a spring-biased metal clip having jaws biased to releasably grip the non-insulated surgical instrument.

19. A system as defined in claim 14, wherein the instrument connector further comprises a piece of conductive tape.

20. A system as defined in claim 14, further comprising:
a supplemental insulation sleeve adapted to fit over a distal end of the active electrode to prevent current leakage through defects within the active electrode.

21. A system as defined in claim 14, wherein the electrosurgical generator includes a contact quality monitor, and the primary return electrode has two patient contacts between which a signal is conducted through the patient by the contact quality monitor to determine the quality of the contact between the patient and the primary return electrode, and wherein:
the separation of the auxiliary return electrode from the primary return electrode prevents the burn-producing current from interfering with the signal conducted between the two patient contacts of the primary return electrode during operation of the contact quality monitor.

22. A system as defined in claim 14, wherein:
the instrument connector is adapted to rotate freely about the non-insulated surgical instrument while maintaining contact between the conductive surface and the non-insulated surgical instrument.

23. A system as defined in claim 14 further comprising:
a plurality of instrument connectors and attached instrument leads to connect a plurality of non-insulated surgical instruments inserted within the patient cavity to the auxiliary electrode.

24. A system as defined in claim 23, further comprising:
a plastic cannula adapted to be inserted through a patient wall to provide a guide for insertion of each non-insulated surgical instrument into the patient cavity and to electrically insulate the patient wall from each non-insulated surgical instrument.

25. A system as defined in claim 24, further comprising:
a plastic cannula adapted to be inserted through the patient wall of the patient to provide a guide for insertion of the active electrode into the patient cavity and to electrically insulate the patient wall from the active electrode.

26. A system as defined in claim 14, wherein the instrument connector further comprises:
a rounded end portion defining a channel for insertion of the non-insulated surgical instrument; and
a tapered end portion attached to the rounded end portion, said tapered end portion attached to an end of the instrument lead.

27. A system as defined in claim 26, wherein:
the rounded end portion of the instrument connector includes a plurality of cuts which define a plurality of flaps;
said flaps resiliently deflect against the instrument to form the channel and establish an electrical contact with the instrument.

28. A system as defined in claim 26 wherein the electrically conductive surface further comprises:
a layer of aluminum deposited upon a top surface of both the rounded end portion and the tapered end portion of the instrument connector.

29. A system as defined in claim 28, wherein:
the rounded end portion of the instrument connector includes a plurality of cuts which define a plurality of flaps;
a top surface of the flaps contains the deposited layer of aluminum;
the flaps are forced open by the distal end of the non-insulated surgical instrument to define the channel for insertion of the instrument through the rounded end portion of the instrument connector; and
a portion of the top surface of the flaps remains in contact with the non-insulated surgical instrument when the distal end of the instrument is inserted through the channel from the top surface of the rounded end portion of the instrument connector.

30. A system as defined in claim 29, wherein an end of the instrument lead is attached to the layer of aluminum deposited on the top surface of the tapered end portion of the instrument connector.

* * * * *